United States Patent [19]
Bentley et al.

[11] 4,248,828
[45] * Feb. 3, 1981

[54] OXYGENATOR

[75] Inventors: Donald J. Bentley, Newport Beach; Donald A. Raible, Orange, both of Calif.

[73] Assignee: Bentley Laboratories, Inc., Irvine, Calif.

[*] Notice: The portion of the term of this patent subsequent to Nov. 15, 1994, has been disclaimed.

[21] Appl. No.: 780,077

[22] Filed: Mar. 22, 1977

Related U.S. Application Data

[63] Continuation of Ser. No. 565,043, Apr. 4, 1975, Pat. No. 4,058,369, which is a continuation-in-part of Ser. No. 436,913, Jan. 28, 1974, abandoned.

[51] Int. Cl.$^3$ .............................................. A61M 1/03
[52] U.S. Cl. ............................... 422/47; 128/DIG. 3; 422/46
[58] Field of Search ............... 23/258.5 B, 258.5 BH; 128/DIG. 3; 261/DIG. 28; 195/1.8

[56] References Cited

U.S. PATENT DOCUMENTS

| | | | |
|---|---|---|---|
| 3,488,158 | 1/1970 | Bentley et al. | 23/258.5 |
| 3,578,411 | 5/1971 | Bentley et al. | 23/258.5 |
| 3,615,238 | 10/1971 | Bentley et al. | 23/258.5 |
| 3,729,377 | 4/1973 | Leonard | 23/258.5 |
| 3,807,958 | 4/1974 | Bramfield et al. | 23/258.5 |

FOREIGN PATENT DOCUMENTS

| | | | |
|---|---|---|---|
| 1065140 | 9/1959 | Fed. Rep. of Germany | 23/258.5 |
| 1078288 | 3/1960 | Fed. Rep. of Germany | 23/258.5 |

*Primary Examiner*—Michael Marcus
*Attorney, Agent, or Firm*—Lyon & Lyon

[57] ABSTRACT

A blood oxygenating device of the type having an oxygenating chamber, a settling chamber, and a heat exchange chamber. A bubbler assembly within the oxygenating chamber including a housing with blood and oxygen inlet means, an outlet opening for blood bubbles which extends 360 degrees around the bubbler assembly housing, and a continuous closed passageway therebetween for effecting optimum oxygen-carbon dioxide exchange. Blood bubbles pass from the outlet means through a defoamer unit for debubbling. A defoamer support member on the outside of the bubbler assembly housing supports the defoamer unit and affords an open passageway for blood bubbles to flow from the outlet means downwardly adjacent the outside of the bubbler assembly housing into the defoamer unit. The blood, after passing through the defoamer unit, flows first into the settling chamber and then along a divided annular path through the heat exchange chamber for the transfer of heat thereto.

4 Claims, 5 Drawing Figures

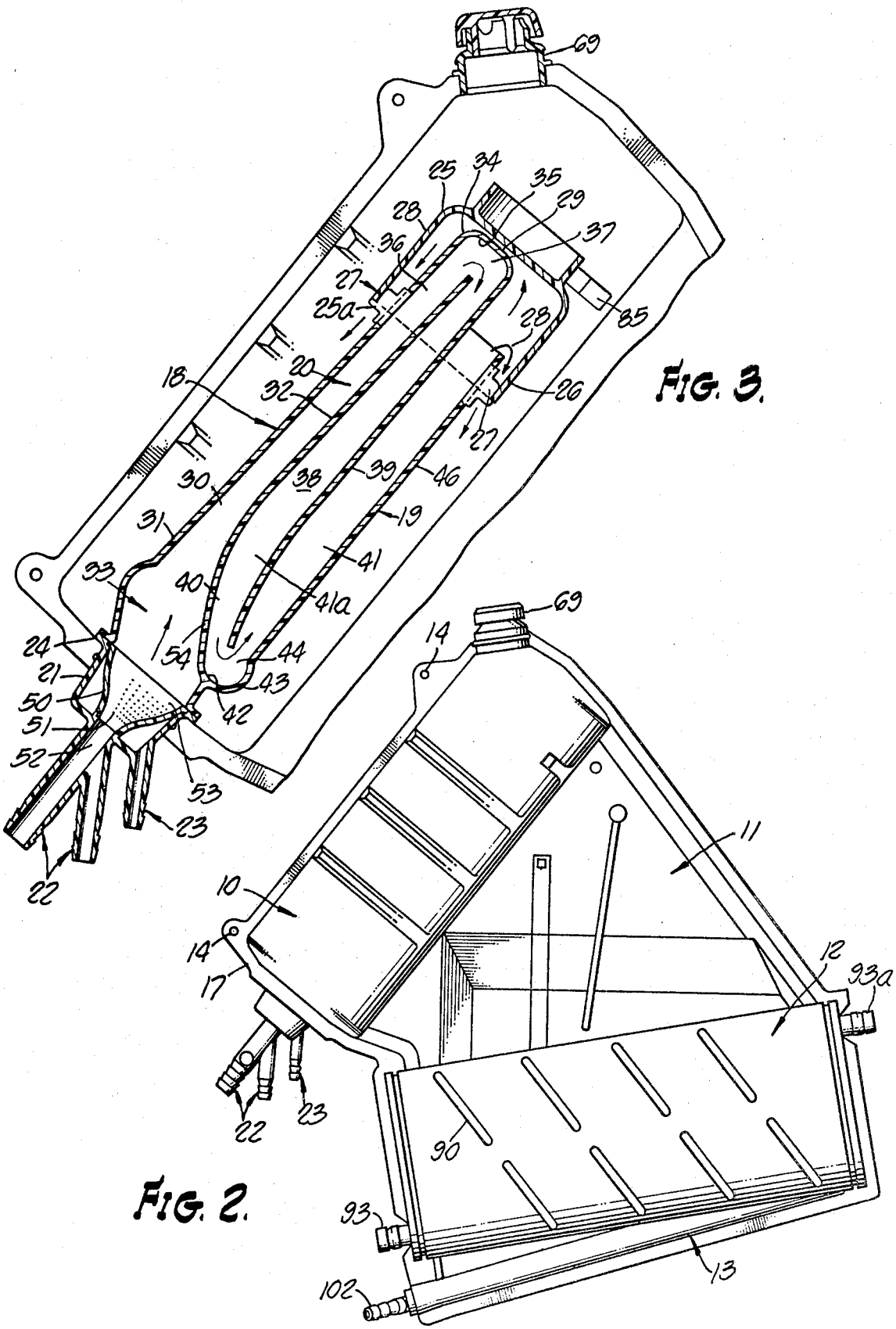

OXYGENATOR

This application is a continuation of application Ser. No. 565,043, filed Apr. 4, 1975, now U.S. Pat. No. 4,058,369, which in turn is a continuation-in-part of our co-pending application, Ser. No. 436,913, filed Jan. 28, 1974 now abandoned, and entitled "Oxygenator."

The invention herein relates to a bubble-type oxygenator of the kind used in thoracic surgery, and more particularly to an oxygenator having improved blood and blood bubble flow characteristics and overall improved operating performance.

The present invention is a further improvement of the devices shown in the Bentley U.S. Pat. No. 3,615,238, issued Oct. 26, 1971, entitled "Oxygenator;" the Bentley et al. U.S. Pat. No. 3,578,411, issued May 11, 1971, entitled "Bubbler Assembly for Blood Treating Apparatus;" and the Bentley et al. U.S. Pat. No. 3,488,158, issued Jan. 6, 1970, entitled "Bubbler Assembly for Oxygenator." These previously patented devices each represent important developments in the blood treatment art. However, since these devices temporarily assume the function of the hear and lungs of a patient during certain operations or other treatments of the body, further improvements are desired which will effect within such devices a blood treatment process as equivalent as possible to that natural process effected by the heart and lungs.

One aspect of the human oxygenating process which has heretofore been difficult to duplicate concerns the ratio of oxygen in the blood to carbon dioxide commonly expressed as the physiological ratio of $pO_2$ to $pCO_2$. In the past oxygenator devices were either unable to maintain this $pO_2$ to $pCO_2$ ratio or, in an effort to maintain such a ratio over the range of flow rates required during operation of the devices, have operated inefficiently and/or in a manner which might adversely affect the blood. That is, when an increase in $pO_2$ was desired, it could only be effected by a substantial increase in the flow of oxygen with respect to the flow of blood into the device This situation represents an inefficient operation and risks blood damage.

Similarly important during the blood treatment process is the temperature control of the blood in order that the blood be at a proper temperature when returned to the patient. In the past, the heat exchange units of the oxygenator devices have not at certain flow rates had the desired heat transfer efficiency to entirely satisfy the blood temperature control requirement or, in oxygenator devices other than shown in the above identified patents, have been subject to a heat exchange medium to blood leak which can be particularly detrimental to The invention disclosed in our co-pending application, Ser. No. 436,913, of which this present application is a continuation-in-part, provides for substantially improved results with regard to both the maintenance of the physiological ratio of $pO_2$ to $pCO_2$ and the temperature control of the blood. The present invention incorporates the features of our previous application, Ser. No. 436,913, and in addition provides features which effect improved blood and blood bubble flow and as a result an overall improved oxygenating process.

In particular, the present invention provides for improved flow between the passageway of the bubbler assembly housing and the defoamer unit. Such improved flow avoids the situation in which the nylon cover on the outside of the defoamer unit becomes saturated with blood. When the cover, which partially functions as a means of filtration, becomes saturated or wet, the small openings therein become restricted. If operation of the unit is continued while the cover is in this condition, the pressure within the bubbler assembly will increase, causing free gas to be forced through the nylon cover in excessive quantity, which can cause a foam to form on the outside of the cover and flow down into the bottom portion of the oxygenator "run wet" is the excessive washing off of an anti-foam surfactant of the defoamer unit.

The present invention contemplates a blood oxygenating device whereby (a) oxygen to blood transfer can effectively and efficiently be achieved, while maintaining a desired physiological oxygen to carbon dioxide ratio irrespective of the flow rates of oxygen and blood at which the oxygenator is operating, (b) improved blood and blood bubble flow characteristics can be obtained, and (c) improved temperature control of the blood can be maintained.

The device of the present invention is a molded plastic structure which includes an oxygenating chamber having a generally circular-cylindrical shape, a substantially thin elongate settling chamber in communication with the oxygenating chamber, and a generally circular-cylindrical heat exchange chamber therebelow. The oxygenating chamber includes a bubbler assembly therein with oxygen and blood inlet means at one end and an outlet for the blood bubbles at the other end which is provided with a cap or cover member.

Venous blood entering the bubbler assembly is bubbled by a plurality of small jetting streams of oxygen to form blood bubbles. A continuous, closed passageway, comprising three segments with restricted cross-sectional flow areas, controls the bubble size and directs a constant flow of blood bubbles from the inlet means to the outlet.

The blood bubbles then exit the bubbler assembly through a circular-shaped opening provided by the cap member and pass down the outside of the bubbler assembly through a series of open spaces provided by a defoamer support member between the exterior of the bubbler assembly housing and layers of defoamer material encompassing the housing into a blood reservoir which extends across the lower end of the oxygenating chamber. As the blood bubbles come in contact with the pool of liquid blood, they dissipate to a large degree, being converted to liquid blood and free oxygen and carbon dioxide gases.

These free gases exit the oxygenating chamber through a port provided at the upper end thereof, while the liquid blood passes through the defoamer material and nylon cover or sock and out of the oxygenating chamber to some other portion of the oxygenator. Bubbles which do not immediately dissipate upon contact with the reservoir and which collect thereon are dissipated as they attempt to pass laterally through the defoamer material.

After the blood passes through the defoamer material and cover of the defoamer unit the blood flows into a settling chamber and then subsequently enters the heat exchange chamber. The heat exchange chamber is provided with acutely angled blood passageways about the exterior surface of a water jacket within the water jacket adjacent the interior surface thereof is provided a continuous helical passageway through which the heat exchange medium flows for the transfer of heat to the blood prior to its return to the patient.

The present invention is illustrated by the accompanying drawings in which:

FIG. 2 is a side view of the oxygenator;

FIG. 3 is a side sectional view of the bubbler assembly;

Figure 1:
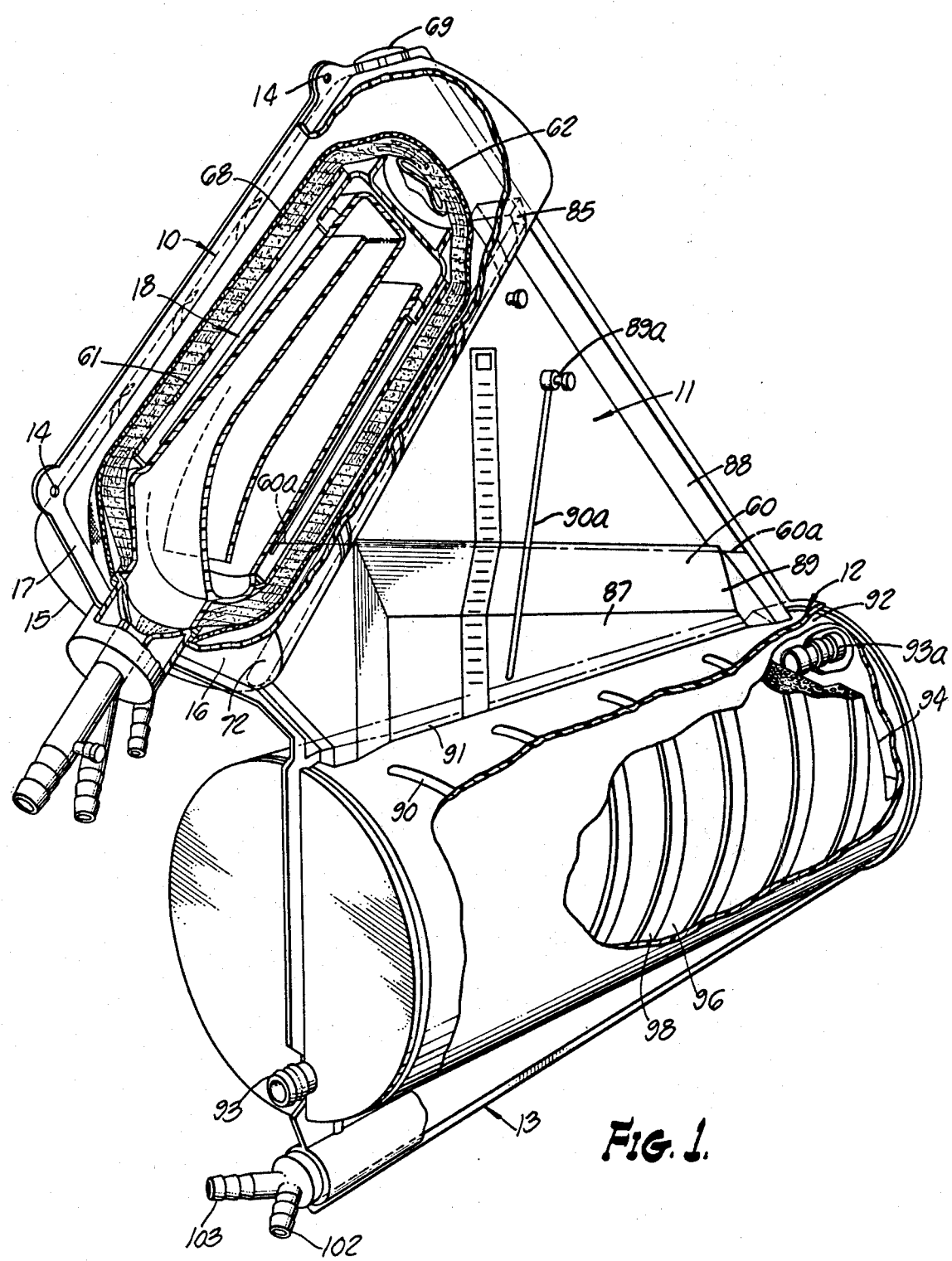
FIG. 1 is a side perspective view partially in section to illustrate the oxygenating chamber and heat exchange chamber.

Referring now in detail to the drawings, the oxygenator device shown includes an upper cylindrical chamber, generally designated 10 (commonly called an oxygenating chamber), a narrow central chamber, generally designated 11, and a lower cylindrical chamber, generally designated 12 (commonly called a heat exchanging chamber), and a collecting chamber, generally designated 13. In use, the oxygenator device may be suspended by hooks or other appropriate means passing through apertures 14 formed at opposite ends of the upper chamber 10. When in normal operation, the angle formed by the axis of the upper cylindrical chamber 10 with the horizontal is preferably in the range of approximately 35° to 40°, and more specifically 37° to 38°.

The chambers 10, 11, 12 and 13 are preferably formed from a polycarbonate plastic (sold by General Electric under the trademark "Lexan") which may either be vacuum formed or injection molded to shape two self-sustaining substantially rigid shells 15 and 16 which are substantially identical with each other except one is the mirror image of the other. The two shells are provided with a coplanar peripheral flange 17, and the peripheral flanges of the two shells are adhered together by a suitable adhesive to form a unitary, transparent structure. The plastic is inert, nontoxic, impervious to the passage of gases and liquids, and sterilizable. It contains no leechable plasticizers which may be traumatic to the blood, and it is exceptionally strong and durable to withstand accidental blows or shocks.

The upper structure or oxygenating chamber 10 includes the bubbler assembly generally designated 18 of the instant invention, which bubbler assembly is preferably mounted so that its longitudinal axis substantially coincides with the longitudinal axis of the cylindrical chamber 10. The function generally of the bubbler assembly is to intermix oxygen gas with incoming venous blood so as to form films of blood in bubble form, which blood bubbles are advanced in oxygen atmosphere through the bubbler assembly to an outlet or outlets. The oxygen atmosphere exists within each of the blood bubbles, and the thin films of venous blood exposed to the oxygen effects a transfer of oxygen gas to the hemoglobin in the blood and the consequent release of carbon dioxide from the hemoglobin of the blood.

In effecting this oxygen-carbon dioxide exchange it is particularly important that there be a thorough intermixing of blood bubbles in the passageway of the bubbler assembly and continuous movement of the blood bubbles throughout the entire passageway to avoid pooling in the passageway. Similarly important is the control of the size of the blood bubbles as they progress through the passageway. The structure of the instant bubbler assembly has proven to be extremely efficient in this regard and has shown a capability of being able to maintain a desired physiological oxygen to carbon dioxide ratio at various flow rates while also maintaining a desired 1/1 ratio of inlet blood to inlet gas or oxygen flow and has further shown a capability of effecting a substantial increase in the transfer of oxygen to blood over the range of both high and low flow rates with a minimum increase of the inlet flow rate of oxygen over the inlet flow rate of blood. Heretofore, at least at certain flow rates, to effect an increase of oxygen transfer to blood required a substantial deviation in the 1/1 ratio inlet oxygen to inlet blood flow rates. As indicated previously, a substantial difference between the rate of inlet blood flow and inlet gas flow is undesirable.

Figure 4:
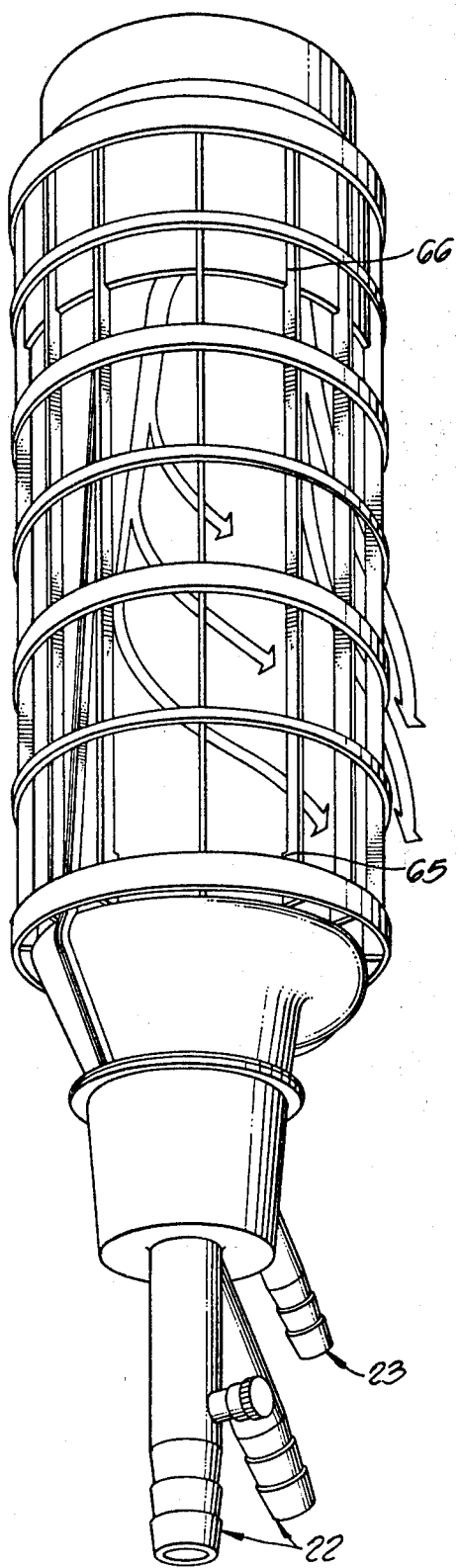
FIG. 4 is a perspective view of the bubbler assembly housing and the defoamer support member illustrating the flow of blood and blood bubbles from the outlet of the housing.

The detailed structure of the bubbler assembly 18 is best shown in FIGS. 1, 3, and 4 and all parts of the bubbler assembly are preferably formed from the polycarbonate plastic material referred to previously. Referring to FIG. 3, the bubbler assembly 18 includes a hollow elongated housing, generally designated 19, which affords an internal chamber defining a continuous closed passageway, generally designated 20. A closure plate 21 carries venous blood inlet means, generally designated 22, and an oxygen inlet means, generally designated 23. The closure plate 21 has a peripheral flange 24 which is adhered to the proximal end of the oxygenating chamber 10 by suitable adhesive to provide an air-tight seal. The other end of the bubbler assembly 18 is covered with a cap or cover member, generally designated 25, which is removably mounted on four tabs, generally designated 25a, affixed circularly 90 degrees apart on the outside of the housing 19. The cover member preferably is generally circularly shaped and is provided with an over-hanging portion 26, which is spaced outwardly of the sides of the housing 19 by the tabs 25a so as to afford outlet means 27 360 degrees around the housing 19 for blood bubbles, generally designated 28. Such an outlet provides for improved flow through the bubbler assembly. The cap member 25, when positioned on the tabs 25a, is approximately one eighth of an inch from the uppermost portion 29 of the bubbler assembly 18. The housing 19 is partitioned so that a continuous closed passageway 20 is divided into a plurality of passageway segments. An upper chamber or passageway segment 30 is defined by a generally rounded upper wall 31 and a generally planar bottom wall 32 which extends from a bubbling chamber 53 at the inlet section 33 upwardly and rearwardly away therefrom to a downwardly returned rounded end portion 34. The interior surface 35 of portion 34 directs fluid from a downstream outlet end 36 of segment 30 into a juncture portion 37 by means of which upper chamber segment 30 is in communication with a vertically adjacent central or intermediate chamber segment 38. The cross-sectional flow area of the passageway 20 which is relatively large at the inlet section 33 smoothly tapers inwardly or decreases as it extends to the outlet end 36 and through juncture portion 37. Fluid is further directed downwardly and forwardly by the segment 38.

Intermediate passageway segment 38 is defined by the generally planar wall 32 and a generally planar lower wall 39. Segment 38 extends from its juncture 37 at the rear in communication with upper segment 30 to a forward outlet end 40 where it joins with a lower segment 41. The cross-sectional flow area of passageway 20 first increases slightly as it extends from its upstream inlet end at the juncture 37 to a mid-section 41a and then decreases as it extends toward the outlet end 40. The interior surface 42 of rounded end portion 43 directs fluid through a juncture portion 44 by means of which chamber segment more particularly juncture portion 44 define a section of the passageway 20 having reduced or restricted cross-sectional flow area which is slightly smaller than the cross-sectional flow area of the passageway 20 at the outlet 36 and juncture portion 37. Fluid is returned rearwardly of chamber segment 41 by the interior surface 42 of rounded rearwardly returned wall portion 43. Lower segment 41 leads away from its juncture at 44 with central chamber segment 38 to the outlet means 27 from the inlet section 33. Lower passageway segment 41 is defined by the generally planar wall 39 and a generally rounded bottom wall 46. The cross-sectional flow area of the passageway 20 in the lower segment 41 increases as it extends from the juncture 44 to provide for a relatively large and unrestricted cross-sectional flow area throughout the length of segment 41.

Thus, blood entering generally through the inlet area will travel an inverted S-shaped path first passing through the upper segment 30, thence being directed downwardly and returned forwardly through the central segment 38 and thence being directed upwardly and returned rearwardly through the lower segment 41 from which it is passed outwardly through outlet means 27. In the sections at the passageway 20 where cross-sectional flow area is decreased, the flow is accelerated therein to insure continuous flow throughout the bubbler assembly and thereby prevent pooling. Moreover, the variations of the cross-sectional flow area of the passageway 20 controls the size of the blood bubbles as they flow through the bubbler assembly. That is, the blood bubbles are the smallest when first formed at the bubbling section where the pressure acting on the blood bubbles, as a result of the downstream bubbles above, is the greatest. As the blood bubbles progress upwardly in the passageway segment 30 the pressure decreases and the size of the bubbles increases. However, as the cross-sectional flow area of the passageway 20 decreases the flow therethrough is constricted and the bubble size is again reduced. Thus, the pattern of the bubble size as the bubbles progress through the bubbler assembly is such: bubble size is the smallest when the bubbles are first formed in the bubbling section 33; bubble size increases as the blood bubbles begin to progress upwardly in the segment 30; bubble size decreases as the blood bubbles move to and through the outlet 36 and juncture 37; bubble size increases as the blood bubbles progress through the segment 38 from the juncture 37 to the mid-section 41a of the segment 38 and then decreases as the blood bubbles progress to and through the outlet end 40 and juncture 44; and finally bubble size increases as the blood bubbles progress from the juncture 44 through the segment 41 to the outlet means 27. This control of the bubble size and in particular the reductions of bubble size as the blood bubbles progress through the passageway 20 is considered to be very important in effecting the desired gas-blood transfer.

At the inlet section 33, a cone-shaped wall member 50 has one portion in which there are arcuately disposed a plurality of minute apertures 51 through which oxygen is admitted into the housing 19. As herein shown, the inner surface of the cone-shaped wall member 50 has 150 apertures, each approximately 0.013" in diameter. The apertures are preferably arranged in increasing arcs in the surface of the cone-shaped wall member 50, there being six arcs of varying radii and 25 apertures in each arc.

As can be seen in FIG. 1, the inner surface of the cone-shaped wall member 50 actually provides a divergent mouth for the inlet port 52 of the blood inlet means 22 so that, as the incoming venous blood diverges in a wide shallow stream, the blood is immediately bubbled by the multitude of tiny jetting streams of oxygen directed transversely of the flow of blood. The structural arrangement is such that substantially all of the incoming blood is immediately formed into bubble films so that complete exposure of the blood in film form to an oxygen atmosphere is immediately accomplished.

As seen in FIG. 3, the housing 19 is upwardly inclined when in operative working position. The blood bubbles initially formed in the bubbling chamber 53 are guided upwardly by inclined surface 54 into the upper passageway segment 30. Within segment 30 some bubbles may burst and reform droplets of blood while still other small quantities or droplets of blood may be carried along in the upward progress of the bubbles blood in the segment 30. However, as droplets of blood form, the droplets gradually gather together and flow back downward by gravity into the bubbling chamber 53 once more where the blood is again rebubbled and moved once more up the passageway segment 30.

As the blood bubbles pass through the outlet means 27 of the bubbler assembly 18, the bubbles flow down the outside of housing 19 to liquid blood reservoired in the oxygenating chamber 10. The level of this reservoired blood is identifcal to that in the blood reservoir 60 of the central chamber 11 and is approximately indicated by the phantom line 60a shown in FIG. 1. Some of the bubbles may dissipate and form droplets of blood as they flow down the outside of housing 19, while other bubbles may dissipate as they contact the liquid blood reservoired at the lower end of the oxygenating chamber.

Figure 5:
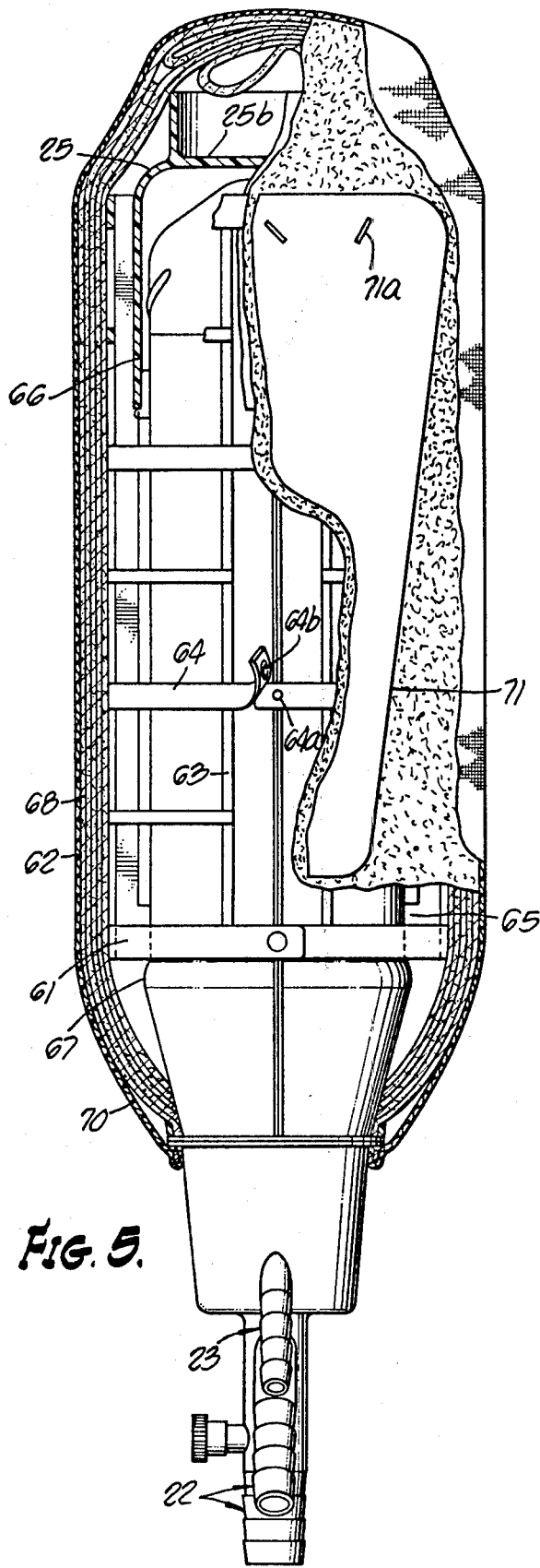
FIG. 5 is a bottom view of the interior of the oxygenating chamber to illustrate the placement of the defoamer support member and splash shield.

Referring to FIGS. 1 and 5, situated on the outside of the bubbler assembly 18 is a defoamer support means 61 which provides the space between the bubbler assembly 18 and defoaming means 62 for the blood bubbles to freely pass from the outlet means 27 to the reservoired blood. This defoamer support means 61 is preferably constructed of polypropylene in a lattice-work fashion, having a plurality of spacing segments 63 parallel to each other and a plurality of holding bands 64, which are parallel to each other, but affixed to the spacing segments 63 perpendicular thereto with such holding bands 64 fixedly positioned at each end of the spacing segments 63. Certain of the holding bands 64 are longer than others and have pins 64a affixed to ends thereof, which extend radially out from the longitudinal axis of the chamber 10, and holes 64b in the other ends to accomodate said pins 64a. This arrangement allows for the defoamer support means to be fastened into place when wrapped around the outside of the bubbler assembly 18 by snapping the pins 64a into the holes 64b.

As shown in FIG. 4, the spacing segments 63 are preferably so constructed as to have one side which incorporates a seating extension 65 at one end and a cap indentation 66 at the other end. The other three sides of the spacing segments 63 are flat and the holding bands 64 lie across the flat side of each spacing segment 63 opposite the seating extensions 65 and the cap indentations.

As shown in FIG. 5, the defoamer means 61 is wrapped around the bubbler assembly 18 with the spacing segments 63 running parallel to its longitudinal axis and with the holding bands 64 circumscribing the bubbler assembly 18 perpendicular to its longitudinal axis. The only portions of the defoamer support means 61 that contact the bubbler assembly housing 19 are the seating extensions 65, which do so at the lower end of the bubbler assembly housing 19 at a bulging portion 67 thereof, which provides a restricting surface upon which the seating extensions 65 rest, holding the defoamer support means 61 in its desired position relative to the bubbler assembly 18. The cap indentations 66 at the upper end of the defoamer support means 61 provide an opening whereby the cap member 25, which covers the top of the bubbler assembly 18, can be placed in its operating position between the defoamer support means 61 which extends to approximately the top wall 25b of the cap member 25 when the oxygenating chamber 10 is in its fully assembled configuration.

The defoamer support means 61 is held in position around the bubbler assembly 18 by the defoaming means 62, which it supports away from the bubbler assembly housing 19 approximately one half inch. The defoaming means 62 is preferably formed in the shape of a sleeve which is closed at one end, fits over the outer lateral surface of the defoamer support means 61 and has a draw string at its open end which is drawn tightly around the bubbler assembly 18 so that all the blood flowing out of the bubbler assembly 18 will be caused to flow through the defoaming means 62. The sleeve is constructed of a plurality of similarly shaped sleeve layers 68 of knitted mesh material, which layers are nested one within another to provide a multitude of tortuous paths of flow. The knitted layers 68 are preferably formed of polypropylene fibers (polyurethane foam also being acceptable) each of which is generally smooth and round and presents no rough surfaces (which may cause damage to the red blood cells) to the flow of blood passing therethrough. The polypropylene layers 68 are impregnated or coated with a non-toxic antifoam composition of the medical silicon antifoam type which is well known in the art.

Thus, as blood bubbles collect on the surface of the reservoired blood and move outwardly on the surface, they contact the defoaming layers and rivulets of oxygenated blood are formed, freeing oxygen and carbon dioxide which ultimately escape through port 69 (shown in FIG. 1) provided for such purpose near the top of the oxygenating chamber 10. The same is true for any blood bubbles that might contact the defoaming means 62 before reaching the reservoir 60.

As shown in FIG. 5, a porous bag 70 covers the defoaming means 62 in the same way that the defoaming means covers the defoamer support means 61, and has a draw string at its open end, which is drawn tightly around the bubbler assembly 18 so that all the blood and gas flowing out of the bubbler assembly 18 will be caused to pass through the bag 70. This bag 70 aids in holding the defoaming means 62 and defoamer support means 61 in place. Also, the bag 70, preferably formed of nylon material and having a pore size of about 150 microns, filters blood as it exits the bubbler assembly 18. In the adult size oxygenator, the bag 70 preferably has a surface area of approximately 144 sq.in. Also, in the adult size oxygenator, it is preferred to provide about 4 or 5 layers 68 of the polypropylene fabric, while in the pediatric and infant size the number of layers may be decreased.

Between the defoaming means 62 and the porous bag 70, a polyethylene sheet 71 is positioned so as to extend about the bottom of the bubbler assembly 18 for nearly 120 degrees. The arcuately disposed lower marginal edge of the polyethylene sheet 71 is normally positioned about four inches upwardly of the lower end of the oxygenating chamber 10, and the upper arcuate marginal edge of the sheet 71 extends beyond the cap member top wall 25b. This sheet 71 is fastened to the defoaming means 62 by tack-like buttoneers 71a which have barbed ends that pass through the sheet 71 and extend into the defoaming means 62. The purpose of the polyethylene sheet 71 is to form a troughlike formation for any debubbled blood passing through the defoaming means 62 before reaching the reservoired blood in the oxygenating chamber 10. Thus, the sheet 71 causes such debubbled blood to flow angularly downwardly through the defoaming means 62 within the sheet 71, which helps maximize the debubbling operation, and the sheet 71 causes the blood to gradually flow to the lower end of the oxygenating chamber 10 so as to make a smoother exit therefrom through exit opening 72 shown best in FIG. 1. Normally, debubbled blood is collected just past opening 72 and if sheet 71 were not present, some of the debubbled blood from the oxygenating chamber 10 might drip down and splash on such collected blood, causing undesirable bubbling.

The excess free oxygen from the bubbling operation and the oxygen and carbon dioxide emitted in the debubbling or defoaming operation escape from the oxygenating chamber 18 through port 69. As best seen in FIG. 1, at least a pair of arcuate indented ribs 85 center the bubbler assembly with respect to the oxygenating chamber and away from the interior surfaces thereof. Thus, gases are free to escape outwardly through the nylon bag 70, then upwardly to the top of the oxygenator chamber 10, and finally longitudinally outwardly to the port 69.

Short indentations (not shown) are preferably formed at the lower end of the chamber 10 to afford supports for the nylon bag and thereby space the bag from the elongated, narrow, exit opening 72, which is the open upper end of the central chamber 11. Thus, the nylon bag when wetted with blood will be prevented from lodging in sealing engagement with the exit opening 72.

The narrow central or intermediate chamber 11 provides the reservoir 60 for the oxygenated blood. The central chamber has sidewall portions 87 (only one of which is shown) which are generally parallel and rather closely spaced. The sidewall portions 87 are joined to the large sidewall portions 88 (only one of which is shown) by diverging portions 89 (only one of which is shown). The sidewall portions 88 are also generally parallel but, because of the diverging sidewall portions 89 are spaced farther apart than are the sidewall portions 87. Thus, the lower end of the central chamber or reservoir 11 accommodates a small volume of oxygenated blood and will fill rather rapidly in use so that during use the hevel of the blood will preferably extend into the lower end of the upper oxygenating chamber 10. Arterial sampling port 89a located above the normal blood level within the central chamber 11 communicates with tube 90a which extends into the blood in the blood reservoir 60 and provides for the addition of medicaments and other liquids thereto without splashing.

The lower mating portion of shells 15 and 16 afford the lower cylindrical chamber 12, and the shell portions are provided with indented pairs of arcuate but broken ribs 90, the corresponding pairs in each shell portion being positioned in a plane extending at an acute angle to the axis of the lower chamber 12, as shown in FIG. 2. The central chamber 11 communicates with the cylindrical chamber 12 through a narrow elongated slot extending substantially the full length of the chamber 12.

The lower chamber 12 houses a water jacket 92 which makes a close fit with and abuts the arcuate ribs 90 so as to arcuately provide a number of wide, shallow passages for blood flow between the outer surface of the waterjacket 92 and the inner surfaces of the shells 15, 16, the depth of the passages preferably being on the order of 0.065 to 0.080 inches.

The water jacket 92 is hermetically sealed and inlet fitting 93 and outlet fitting 93a are provided for flowing through the heat exchanging chamber 12 temperature control liquid so as to control the temperature of the wide, thin steams of oxygenated blood passing over the outer surface of the water jacket. In the adult size oxygenator, the heatexchanging surface of the jacket 92 preferably has an area of approximately 270 sq.in.

Within the water jacket 92 is a core 94, preferably formed of styrofoam. The inlet fitting 93 communicates with a continuous passageway 96 about the core and adjacent the interior surface of the jacket. The passageway 96 which communicates with the outlet fitting 93a is defined by a continuous helical rib 98 of the core which seals with the interior surface of the jacket. This defined structure of the heat exchange chamber provides for a particularly efficient heat transfer between the blood and the temperature control medium, in this instance water. That is, the shallow passageway 96 effects an increase in velocity of the water therethrough thereby providing through the heat exchange surface medium at a higher temperature than if the medium progressed slowly across the heat exchange surface.

In addition to defining wide, shallow passages, the ribs 90 function as a bubble trap for any gas bubbles which might be carried through the blood outlet fittings 102 and 103 to the arterial system of the patient.

In operating, blood enters the oxygenating chamber 10 through blood inlets 22 and oxygen is fed into the oxygenating chamber through inlet 23. The blood and oxygen are intermixed and travel through the tortuous passageway in the interior of the bubbler assembly 18 and, particularly, through upper segment 41 and finally through the port defined by the cap member. After passing through port or outlet, the blood passes outwardly and downwardly of the exterior of the bubbler housing 19 to the reservoired blood and through the defoaming means and then into the central chamber 11.

In central chamber 11, the blood is held in a generally sheet-like column and flows therefrom by means of opening 91 into the heat exchange chamber 12 in a divided annular path around the water jacket 92. The blood travels in the shallow passages which are acutely angled relative to the axis of the heat exchange chamber and the blood bubbles tend to rise upwardly along ribs 90. From the heat exchange chamber, the blood travels to the blood-collecting chamber 13 from which it may be returned to a patient through discharge ports in fittings 102 and 103.

As a result of this invention, a blood oxygenator can effectively and efficiently transfer oxygen to blood, while maintaining a desired physiological oxygen to carbon dioxide ratio irrespective of the flow rates of oxygen and blood at which the oxygenator is operating. Further, this invention provides for enchanced flow characteristics, by which the possibility of "running wet" is avoided, as well as providing for better temperature control of the oxygenated blood.

Having fully described the invention, it is to be understood that the invention herein is not limited to the details of the embodiments herein set forth nor to the details illustrated in the drawings, but the invention is of the full scope of the appended claims.

We claim as our invention:

1. A blood oxygenating device having a bubbler assembly for forming films of blood in bubble form by directing oxygen into a stream of venous blood and causing the transfer of oxygen to the films of blood and the release of carbon dioxide from the films of blood, said bubbler assembly, including a defoaming means for defoaming bubbled blood wrapped around said bubbler assembly such that all blood and gases flowing out of said bubbler assembly pass through said defoaming means wherein the improvement comprises:

a plurality of ribs spaced-apart around said assembly and disposed along the length of said assembly, said ribs positioned between said defoaming means and said bubbler assembly for supporting said defoaming means a predetermined distance from and out of contact with the outside wall of said bubbling assembly and affording a passageway for blood bubbles between the outside wall of said bubbler assembly and said defoaming means.

2. A blood oxygenating device having a bubbler assembly with a passageway for forming films of blood in bubble form by directing oxygen into a stream of venous blood and causing the transfer of oxygen to the films of blood and the release of carbon dioxide from the films of blood, said passageway having a plurality of sinusoidally arranged segments serially disposed in end to end relationship, a first one of said segments being adjacent to the oxygen inlet end of said passageway and having a progressively reduced cross-sectional flow area extending along a substantial portion of its length, a second one of said segments in communication with said first segment which second segment has an initial portion of greater cross-sectional flow area than the downstream end of said first segment and a further portion having a cross-sectional flow area smaller than any portion of said first segment, said reduced cross-sectional flow area of said first segment and said further portion of said second segment being effective to accelerate the flow of bubbles therethrough and control the size of bubbles in said passageway.

3. The device of claim 2 wherein said passageway has three segments.

4. The device of claim 2 wherein said device has a rigid shell.

* * * * *